United States Patent
Schiweck et al.

[11] 4,117,173
[45] Sep. 26, 1978

[54] USE OF GLUCOPYRANOSIDO-1,6-MANNITOL AS A SUGAR SUBSTITUTE

[75] Inventors: Hubert Schiweck, Obrigheim; Georg Steinle, Grünstadt; Lutz Müller; Wolfgang Gau, both of Wuppertal; Mohammad Munir, Obrigheim, all of Germany

[73] Assignee: Suddeutsche Zucker-Aktiengesellschaft, Mannheim, Germany

[21] Appl. No.: 682,674

[22] Filed: May 3, 1976

[30] Foreign Application Priority Data

May 6, 1975 [DE] Fed. Rep. of Germany ....... 2520173

[51] Int. Cl.² .............................................. A23L 1/236
[52] U.S. Cl. .................................... 426/548; 426/658; 426/804; 536/4
[58] Field of Search ...................... 426/548, 658, 804; 536/4; 260/635 C

[56] References Cited

U.S. PATENT DOCUMENTS 3,865,957  2/1975  Schiweck .......................... 426/548

FOREIGN PATENT DOCUMENTS 1,169,433  5/1964  Fed. Rep. of Germany .............. 536/4
1,022,480  3/1966  United Kingdom ................. 260/535 C

OTHER PUBLICATIONS

Manners et al., Carbohydrate Research, 7(3), (1968), pp. 291-298.

Primary Examiner—Raymond N. Jones
Assistant Examiner—Esther M. Kepplinger
Attorney, Agent, or Firm—Armstrong, Nikaido, Marmelstein & Kubovcik

[57] ABSTRACT

Glucopyranosido-1,6-mannitol, represented by the formula:

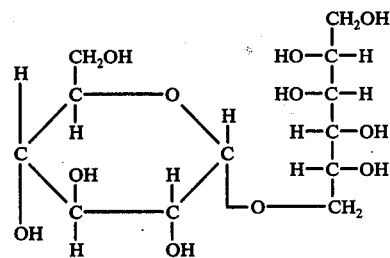

and a process for its preparation are provided. The glucopyranosido-1,6-mannitol is obtained by catalytically hydrogenating neutral aqueous solutions of isomaltulose and cooling the hydrogenated solution.

In a second embodiment of the invention the use of the glucopyranosido-1,6-mannitol as a sugar substitute, sweetener for food or beverages, and sweetened food composition is provided.

5 Claims, 1 Drawing Figure

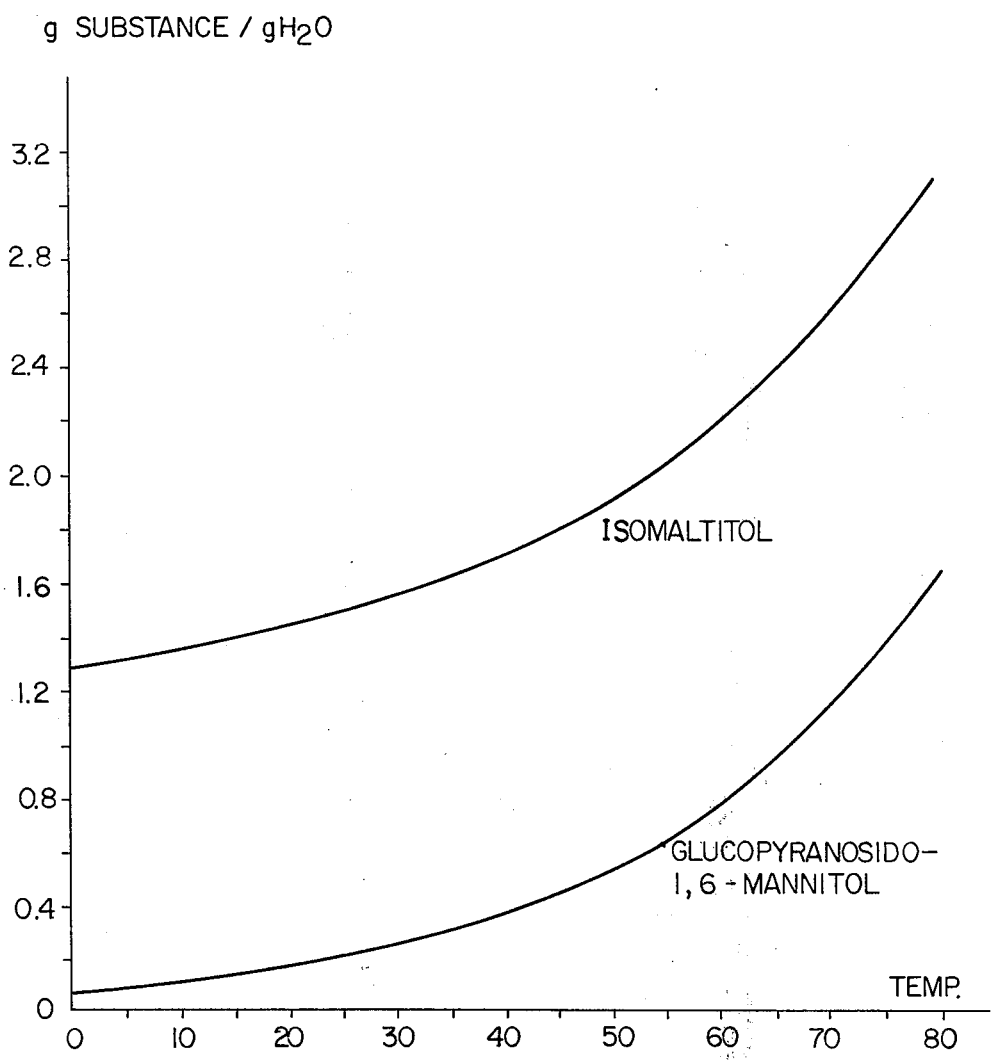

USE OF GLUCOPYRANOSIDO-1,6-MANNITOL AS A SUGAR SUBSTITUTE

BACKGROUND OF THE INVENTION

1. Field of the Invention

The present invention relates to glucopyranosido-1,6-mannitol, a process for producing the same from isomaltulose and its use as a sugar substitute.

2. Description of the Prior Art

In United States Patent Application No. 652,543, filed Jan. 26, 1976 now abandoned, there is disclosed a process for producing isomaltitol. The isomaltitol is produced by catalytically hydrogenating isomaltulose under alkaline conditions.

SUMMARY OF THE INVENTION

According to the present invention glucopyranosido-1,6-mannitol, represented by the structural formula

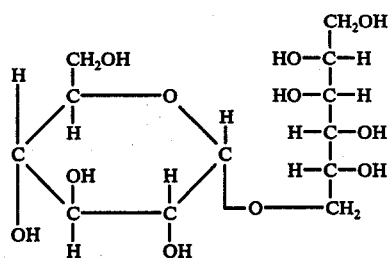

is produced by catalytically hydrogenating aqueous solutions of isomaltulose under neutral conditions, i.e., neutral aqueous solutions of isomaltulose, and separating the desired product from the hydrogenated solution by fractional crystallization.

The glucopyranosido-1,6-mannitol is a valuable dietetic substance which may be used as a sugar substitute or sweetener for food and beverages either alone or in combination with other artificial sweeteners or may be mixed with a variety of sweet-tasting carbohydrates.

BRIEF DESCRIPTION OF THE DRAWING

The drawing shows the solubility of isomaltitol and glucopyranosido-1,6-mannitol as a function of temperature.

DESCRIPTION OF PREFERRED EMBODIMENTS

The hydrogenation of the isomaltulose is carried out according to the process disclosed in application Ser. No. 652,543 (incorporated herein by reference) in the presence of a Raney nickel catalyst and at a temperature of from about 100° to 130° C and at a hydrogen pressure of from about 30 to 100 kg/cm$^2$, but by employing neutral conditions. As the isomaltulose there may be employed, for example, isomaltulose produced according to the process described in the application Ser. No. 652,543 (incorporated herein by reference) or produced according to German Pat. No. 1,049,800.

It has been found that by changing the conditions involved in the hydrogenation of isomaltulose, more particularly, by employing neutral aqueous solutions, the two stereoisomeric forms, i.e., isomaltitol and glucopyranosido-1,6-mannitol, can be obtained in a ratio of approximately 1:1 by weight, and that it is possible to separate both substances from one another by fractional crystallization from aqueous solutions and to produce them in pure form. Owing to the significantly lower solubility of glucopyranosido-1,6-mannitol in the temperature range of 0 - 60°, this substance crystallizes out first (see the drawing).

It was surprising and quite unexpected to find that the glucopyranosido-1,6-mannitol produced in this way, proved to be non-splitable and non-resorbable in an experiment carried out on animals and is thus suitable for use as a sugar substitute for diabetics. Accordingly, it represents a valuable dietetic addition. The following diagram illustrates the course of the reaction according to the invention:

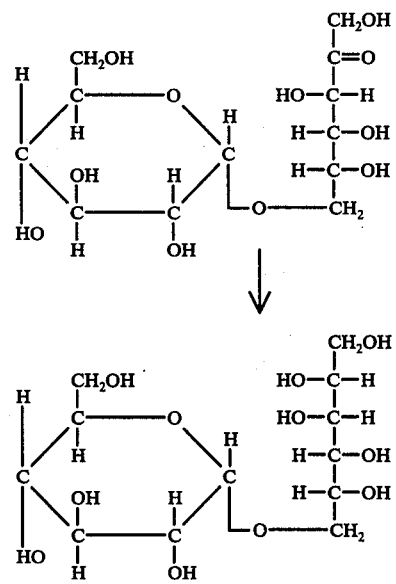

In the process according to the invention, the hydrogenation of isomaltulose can be carried out with a higher dry substance content (60 - 70%) than in the process described in application, Ser. No. 652,543, in that after hydrogenation, the catalyst is removed by decanting or centrifuging still in the heated state at about 80° C and glucopyranosido-1,6-mannitol is caused to crystallize immediately from this solution by cooling. In this way it is possible to largely eliminate the complete deionization of the hydrogenated solution and the subsequent evaporation of the fully deionized hydrogenated solution. The water evaporation which is still required then only amounts to about 30%, as in the process according to application, Ser. No. 652,543.

After the catalyst has been separated from the hydrogenated solution, in the process according to the invention the hydrogenated solution is cooled in a cooling tub at a cooling rate of 0.5° - 2°/hour under constant agitation. To improve crystallization of the glucopyranosido-1,6-mannitol, stimulating crystals are added to the solution at approximately 70° C in quantities of approximately 5 - 10% relative to the solids content of the solution. After cooling to approximately 30° C, that is, after a crystallization period of 24 - 48 hours, glucopyranosido-1,6-mannitol is separated from the crystal suspension on wire basket centrifuges and the mother liquor is then subjected to crystallization by evaporation to obtain isomaltitol.

The glucopyranosido-1,6-mannitol separated by centrifuging is again recrystallized from an aqueous solution to obtain the substance in chemically pure form. Recrystallization of the glucopyranosido-1,6-mannitol is effected by producing a saturated solution at 80° C and subsequently producing crystallization by cooling it in a cooling tub, again at a cooling rate of 0.5 – 2° C/hour. The glucopyranosido-1,6-mannitol which crystallizes out is separated on a wire basket centrifuge and dried in a hot air current.

Although the product, which is thereby obtained, is free flowing and appears completely dry, it has a water content of 5 – 7% and a melting point of 103° – 125° C. The exact melting point of the anhydrous product can be obtained, for example, by allowing the water-containing product to melt in a vacuum drying oven at 105° C and 15mbar and by evaporating the water from the melt. This process takes approximately 4 – 5 hours and the melt then begins to recrystallize. A sample treated in the above manner has a water content of <0.1% and a melting point of 173.5° C.

Specific rotation $\alpha_D^{20} = + 90.5°$ ($c = 2$ in water).

Isomaltitol can be obtained from the mother liquor of the first fractional crystallization by crystallization through evaporation at approximately 100 – 200 mbar by evaporating the solution to an approximately 75% solids content, inoculating the solution with crystals and continuing crystallization until a solids content of 85% is obtained in the crystal suspension.

This takes 8 – 10 hours. The crystal suspension is then placed in a cooling tub and cooled to 30° C at a cooling rate of 0.5 – 2°/hour. The crystal suspension is separated on a wire basket centrifuge and the mother liquor subjected to another crystallization step. The isomaltitol thereby obtained is recrystallized from the aqueous phase and recovered by centrifuging. Upon being dried in a hot air current the isomaltitol has a water content of 0.5%. The constants for the isomaltitol has a water content of 0.5%. The constants for the isomaltitol after it has been dried in a vacuum drying oven at 105° C and 15 mbar are the following:

Melting point = 168° C
Specific rotation $\alpha_D^{20} = + 90.5°$ ($c = 2$ in water)

The melting points of the two substances were determined in a TOTTOLI melting point determining device, a temperature increase of 5° C/minute being maintained.

As the normal physical data which are used to describe substances are very similar in the case of isomaltitol and glucopyranosido-1,6-mannitol, both substances were also characterized more specifically by their nonaacetates:

Glucopyranosido-1,6-mannitol-Nonaacetate

Melting Point = 105.5° – 109.2° C (fusomat)
Specific rotation ($c = 1.1$ in chloroform)
$[\alpha]_D^{20}\ 589 = + 91.5°$
$[\alpha]_{Hg}^{20}\ 578 = + 95.5°$
$[\alpha]_{Hg}^{20}\ 546 = + 108.2°$
$[\alpha]_{Hg}^{20}\ 436 = + 180.5°$
$[\alpha]_{Hg}^{20}\ 365 = + 304.4°$ Isomaltitol - Nonaacetate Melting point = 112.0° – 115.2°C (fusomat)
Specific rotation ($c = 1.1$ in chloroform)
$[\alpha]_D^{20}\ 589 = + 70.4°$
$[\alpha]_{Hg}^{20}\ 578 = + 73.5°$
$[\alpha]_{Hg}^{20}\ 546 = + 83.1°$
$[\alpha]_{Hg}^{20}\ 436 = + 138.6°$
$[\alpha]_{Hg}^{20}\ 365 = + 209.2°$ The drawing is a graph showing the solubility of glucopyranosido-1,6-mannitol and isomaltitol in relationship to the temperature. As indicated in the drawing, the solubility of glucopyranosido-1,6-mannitol is significantly lower than that of isomaltitol but it is adequate, from a technological standpoint, for glucopyranosido-1,6-mannitol to be used as a sweetener for beverages and food.

At room temperature even glucopyranosido-1,6-mannitol solutions containing 1 N acids will not break down. Glucopyranosido-1,6-mannitol breaks down into glucose and mannitol when hydrolysis is carried out in 2 N hydrochloric acid at 100° C for 3 hours. Glucopyranosido-1,6-mannitol is thus very stable in its resistance to acids which is important as far as further processing is concerned.

Glucopyranosido-1,6-mannitol is not caused to ferment by yeast. Neither will glucopyranosido-1,6-mannitol be broken down at room temperature by commercially used preservative additives or by purified glucosidases. On the basis of these findings it may be assumed that glucopyranosido-1,6-mannitol will not be broken down by the glucosidases anchored in the mucous tissues of the human intestine (small) and that consequently it will not be resorbed. The hypothesis of the stability and non-resorbability of glucopyranosido-1,6-mannitol has been confirmed by experiments with rats wherein solutions of glucopyranosido-1,6-mannitol solutions were injected directly into the small intestine of the rats and changes in the contents of glucose, fructose, and mannitol in the blood were measured in relation to the passage of time. No substantial increase in the glucose content of the blood was established upon administration of glucopyranosido-1,6-mannitol. Even after consumption of up to 100 g glucopyranosido-1,6-mannitol in the morning on an empty stomach, test subjects having a healthy metabolism showed no change in the blood level and neither was there an output of insulin. As glucopyranosido-1,6-mannitol is not resorbed it is thus a sweet-tasting, readily water-soluble, structure-forming, texture-forming and body-forming additive in foods, food supplements and beverages which are also suitable for diabetics.

In comparative tests conducted with several groups numbering from 15–30 people each, the sweetening power of glucopyranosido-1,6-mannitol was established as being at 45% that of sucrose. The sweetening power was established by comparison with aqueous sucrose solutions of 7% to 8% strength in a triangular test. The taste pattern of glucopyranosido-1,6-mannitol is very similar to that of sucrose. It was difficult to establish valid statistics in the differentiation between solutions of glucopyranosido-1,6-mannitol and sucrose. The sweetening flavor of glucopyranosido-1,6-mannitol is gentle and without an extraneous or after-taste.

Occasionally it may be desirable to vary these properties of glucopyranosido-1,6-mannitol. To achieve this, according to the present invention, glucopyranosido-1,6-mannitol may be mixed with other non-caloric sweeteners such as isomaltitol, maltitol, lactitol, etc. In the case of mixtures of glucopyranosido-1,6-mannitol with isomaltitol, after complete deionization in an ion exchanger, the hydrogenated solution is immediately dried (spray dried, roller dried, freeze dried). Alternatively, the mixture of the two substances can be recovered in crystalline form from the hydrogenated solution after separation of the catalyst, by the crystallization through an evaporation method. The hydrogenated, fully deionized solution can also be used in fluid form, as only traces of sorbitol are formed during hydrogenation.

To increase the sweetening power of glucopyranosido-1,6-mannitol to that of sucrose or even further, according to the invention glucopyranosido-1,6-mannitol, in its solid form, may be easily combined with such artificial sweeteners as benzoic acid sulfimide, cyclohexylsulfamate or phenylalanine-aspartic acid methylester, either in a mixture or chemically bonded. Solutions of glucopyranosido-1,6-mannitol enriched by artificial sweeteners may be used in combination either in dry form (spray drying process, roller drying, or freeze drying), or they may be employed directly.

Likewise, according to the invention, glucopyranosido-1,6-mannitol in either solid or fluid form, may be mixed with a variety of nourishing, sweet-tasting carbohydrates such as fructose, xylitol and sorbitol, to bring the sweetness of the mixture to approximately that of sucrose; in the case of fructose, the ratio is 1:1 by weight.

In the preparation of foods and beverages in the household, for example in baking, preserving, and jellying operations, as well as in the industrial preparation of foods, food supplements and beverages, glucopyranosido-1,6-mannitol can be used pure or as a glucopyranosido-1,6-mannitol-based sweetener in combination with other sweeteners. It can be used in the same way as natural beet or cane sugar.

EXAMPLE 1

6.5 kg isomaltulose were dissolved in 3.5 kg water at 80° C under constant stirring. The 65% by weight aqueous isomaltulose solution which was thereby obtained was immediately transferred without cooling to a heated autoclave equipped with an agitator and having a capacity of 20 l. In the autoclave the above solution was mixed with an aqueous catalyst suspension containing 500 g Raney nickel catalyst. The autoclave was then closed and the air contained therein displaced by rinsing twice with nitrogen. The nitrogen was then removed by rinsing with hydrogen. The autoclave was then filled with hydrogen at a pressure of 100 kg/cm$^2$ and heated to 120° C under constant agitation. Upon reaching this temperature, the heat was immediately switched off and the autoclave allowed to cool to 80° – 90° C under constant agitation. The time required for the heating and cooling operation was approximately 3 hours. This period of time was sufficient for complete hydrogenation of the isomaltulose. The pH value of the reaction suspension amounted to 7 both before and after hydrogenation. Upon opening the autoclave the content thereof was centrifuged, still at 80° C, and the Raney nickel thus removed. Gas chromatographic testing of the hydrogenated solution after esterification with N,N-Bis-trimethylsilyl-trifluoracetamide showed that glucopyranosido-1,6-mannitol and isomaltitol were present in a ratio of 1:1 by weight and that, apart from these two substances, only traces of sorbitol were formed in the solution.

The glucopyranosido-1,6-mannitol was then allowed to crystallize by cooling. To this end, 300 g glucopyranosido-1,6-mannitol crystals having a grain size of 0.10 – 0.15 mm were added to the solution and the solution was then cooled to 30° C at a cooling rate of 1.5° C per hour. The glucopyranosido-1,6-mannitol crystals were then separated from the mother liquor on a wire basket centrifuge. 1.9 kg glucopyranosido-1,6-mannitol in crystal form were thus obtained. The glucopyranosido-1,6-mannitol was then subjected to another crystallization operation from an aqueous solution and thus further purified.

The mother liquor of the first crystallization which was enriched with isomaltitol was subjected to crystallization through evaporation after being evaporated to a solids content of 75%. A final concentration comprising an 85% solids content was obtained. The time required for crystallization through evaporation was 8 hours. Thereafter, the crystal suspension was cooled to 30° C in a crystallization tub at a cooling rate of 1.5° C/hour and the isomaltitol was obtained therefrom in crystal form by centrifuging in a wire basket centrifuge. The isomaltitol yield was 1.6 kg. The isomaltitol was subjected to another crystallization step from an aqueous solution and thus further purified.

The mother liquor of the second crystallization, which again contained isomaltitol and glucopyranosido-1,6-mannitol in a weight ratio of approximately 1:1, was evaporated to a dry matter content of 75% and upon carrying out another fractional crystallization step, 1.4 kg glucopyranosido-1,6-mannitol were first obtained, and then 1.4 kg isomaltitol.

EXAMPLE 2

In accordance with the process described in Example 1, 7.5 kg isomaltulose were dissolved at 80° C to form a 75% by weight aqueous solution and then transferred to a heated autoclave equipped with an agitator and having a capacity of 20 l. In the autoclave the solution was mixed with an aqueous catalyst suspension containing 500 g Raney nickel. Hydrogenation and crystallization were then carried out as described in Example 1. After a reaction period of 3 hours, the isomaltulose charge had been hydrogenated to form 3.75 kg each of isomaltitol and glucopyranosido-1,6-mannitol. 3.45 kg isomaltitol and 3.45 kg glucopyranosido-1,6-mannitol could then be obtained therefrom in crystal form by means of the fractional crystallization operation described in Example 1.

Although the invention has been described in conjunction with the foregoing preferred embodiments, it is not to be limited thereto, but instead includes all variations and embodiments within the scope and spirit of the appended claims.

What is claimed is:

1. A sweetened food or beverage for human consumption comprising a foodstuff or beverage and glucopyranosido-1,6-mannitol in an amount effective to sweeten said foodstuff.

2. The sweetened food or beverage of claim 1 which further comprises, as a sweetener, isomaltitol.

3. The sweetened food or beverage of claim 1 which further comprises, as a sweetener an artificial sweetener selected from benzoic acid sulfimide, cyclohexylsulfamate and phenylalanineaspartic acid methyl ester.

4. A sweetened food composition which comprises a naturally sweet carbohydrate foodstuff and glucopyranosido-1,6-mannitol, the glucopyranosido-1,6-mannitol being present in an amount effective to sweeten said foodstuff and yield a food composition having the approximate sweetness of sugar.

5. The sweetened food composition of claim 4 where the carbohydrate foodstuff is selected from fructose, xylitol and sorbitol.

* * * * *